United States Patent
Dakka et al.

(10) Patent No.: US 10,414,701 B2
(45) Date of Patent: Sep. 17, 2019

(54) PRODUCTION OF ALKYLATE FROM LIGHT ALKANES

(71) Applicant: ExxonMobil Research and Engineering Company, Annandale, NJ (US)

(72) Inventors: Jihad M. Dakka, Whitehouse Station, NJ (US); Guang Cao, Princeton, NJ (US); Patrick L. Hanks, Bridgewater, NJ (US); James R. Bielenberg, Lebanon, NJ (US); Cynthia F. Omilian, Whitehouse Station, NJ (US); Jessica M. Wittmann, Easton, PA (US)

(73) Assignee: ExxonMoble Research and Engineering Company, Annandale, NJ (US)

( * ) Notice: Subject to any disclaimer, the term of this patent is extended or adjusted under 35 U.S.C. 154(b) by 0 days.

(21) Appl. No.: 15/839,926

(22) Filed: Dec. 13, 2017

(65) Prior Publication Data

US 2018/0162786 A1  Jun. 14, 2018

Related U.S. Application Data

(60) Provisional application No. 62/433,833, filed on Dec. 14, 2016.

(51) Int. Cl.
*C07C 2/86* (2006.01)
*C07C 2/02* (2006.01)
(Continued)

(52) U.S. Cl.
CPC ........... *C07C 2/864* (2013.01); *B01J 29/7038* (2013.01); *B01J 29/80* (2013.01); *C07C 1/24* (2013.01);
(Continued)

(58) Field of Classification Search
CPC .. C07C 2/86; C07C 2/62; C07C 31/12; C07C 31/125; C07C 29/50
See application file for complete search history.

(56) References Cited

U.S. PATENT DOCUMENTS 3,644,565 A  2/1972  Biale
4,384,161 A  5/1983  Huang
(Continued)

FOREIGN PATENT DOCUMENTS

| EP | 0293032 A1 | 11/1988 |
| EP | 0710622 A1 | 5/1998 |
| WO | 9745383 A1 | 12/1997 |

OTHER PUBLICATIONS

Hajimirzaee (Preparation, modification and characterization of selective zeolite based catalysts for petrochemical applications, Apr. 2015, University of Birmingham). (Year: 2015).*

(Continued)

*Primary Examiner* — Youngsul Jeong
(74) *Attorney, Agent, or Firm* — Andrew T. Ward; Priya G. Prasad

(57) ABSTRACT

Systems and methods are provided for forming alkylate from an isoparaffin-containing feed. Olefins for the alkylation reaction can be generated from a portion of the isoparaffin-containing feed. This can be achieved, for example, by using selective oxidation to convert a portion of isoparaffins into alcohol, such as conversion of isobutane to t-butyl alcohol. The alcohol can then be converted to an alkene, such as conversion of t-butyl alcohol to isobutene, in the alkylation reaction environment in the presence of a solid acid catalyst. The solid acid catalyst can then facilitate alkylation of isoparaffin using the in-situ formed alkenes. A catalyst having an MWW framework is an example of a suitable solid acid catalyst.

16 Claims, 5 Drawing Sheets

(51) Int. Cl.

| | | |
|---|---|---|
| *C07C 1/24* | (2006.01) | |
| *C07C 2/12* | (2006.01) | |
| *C07C 2/62* | (2006.01) | |
| *C07C 31/12* | (2006.01) | |
| *C07C 31/125* | (2006.01) | |
| *C07C 29/50* | (2006.01) | |
| *B01J 29/70* | (2006.01) | |
| *C07C 5/02* | (2006.01) | |
| *C07C 29/132* | (2006.01) | |
| *C07C 5/03* | (2006.01) | |
| *C07C 5/27* | (2006.01) | |
| *C07C 407/00* | (2006.01) | |
| *C10G 45/58* | (2006.01) | |
| *C10G 50/00* | (2006.01) | |
| *C10G 69/12* | (2006.01) | |
| *C10G 3/00* | (2006.01) | |
| *B01J 29/80* | (2006.01) | |
| *B01J 29/50* | (2006.01) | |

(52) U.S. Cl.
CPC ............... *C07C 2/12* (2013.01); *C07C 2/62* (2013.01); *C07C 5/02* (2013.01); *C07C 5/03* (2013.01); *C07C 5/2702* (2013.01); *C07C 29/132* (2013.01); *C07C 29/50* (2013.01); *C07C 31/12* (2013.01); *C07C 31/125* (2013.01); *C07C 407/00* (2013.01); *C10G 3/49* (2013.01); *C10G 45/58* (2013.01); *C10G 50/00* (2013.01); *C10G 69/126* (2013.01); *B01J 29/50* (2013.01); *C07C 2523/28* (2013.01); *C07C 2523/34* (2013.01); *C07C 2523/889* (2013.01); *C07C 2529/70* (2013.01); *C10G 2300/104* (2013.01); *C10G 2300/1044* (2013.01); *C10G 2300/1081* (2013.01); *C10G 2300/305* (2013.01); *C10G 2400/02* (2013.01)

(56) References Cited

U.S. PATENT DOCUMENTS

| | | | |
|---|---|---|---|
| 4,439,409 A | 3/1984 | Puppe et al. | |
| 4,826,667 A | 5/1989 | Zones et al. | |
| 4,954,325 A | 9/1990 | Rubin et al. | |
| 5,236,575 A | 8/1993 | Bennett et al. | |
| 5,243,084 A | 9/1993 | Cochran et al. | |
| 5,250,277 A | 10/1993 | Kresge et al. | |
| 5,254,518 A | 10/1993 | Soled et al. | |
| 5,304,698 A | 4/1994 | Husain | |
| 5,340,562 A | 8/1994 | O'Young et al. | |
| 5,362,697 A | 11/1994 | Fung et al. | |
| 5,382,731 A | 1/1995 | Chang et al. | |
| 5,414,145 A | 5/1995 | Sheu et al. | |
| 5,510,309 A | 4/1996 | Chang et al. | |
| 5,523,509 A | 6/1996 | O'Young et al. | |
| 5,719,097 A | 2/1998 | Chang et al. | |
| 6,077,498 A | 6/2000 | Diaz et al. | |
| 6,231,751 B1 | 5/2001 | Canos et al. | |
| 6,376,731 B1 | 4/2002 | Evans et al. | |
| 6,756,030 B1 | 6/2004 | Rohde et al. | |
| 7,713,513 B2 | 5/2010 | Jan et al. | |
| 7,842,277 B2 | 11/2010 | Wieslaw et al. | |
| 7,982,084 B1 | 7/2011 | Moscoso et al. | |
| 8,704,023 B2 | 4/2014 | Wieslaw et al. | |
| 8,704,025 B2 | 4/2014 | Wieslaw et al. | |
| 2014/0243570 A1* | 8/2014 | Nesterenko | B01J 37/10 585/640 |
| 2016/0168048 A1* | 6/2016 | Wang | C10L 1/04 585/310 |
| 2018/0162786 A1 | 6/2018 | Dakka et al. | |
| 2018/0162787 A1 | 6/2018 | Dakka et al. | |
| 2018/0162788 A1 | 6/2018 | Dakka et al. | |
| 2018/0162789 A1 | 6/2018 | Liu et al. | |

OTHER PUBLICATIONS

Albright et al., "Alkylation of isobutane with C4 olefins 1. First-step reactions using sulfuric acid catalyst", Ind. Eng. Chem. Res., 1988, vol. 27, pp. 381-386.

Corma et al., "Chemistry, Catalysts, and Processes for Isoparaffin-Olefin Alkylation: Actual Situation and Future Trends", Cat. Rev. Sci. Eng., 1993, vol. 35, pp. 483-570.

Feng et al., "Catalytic decomposition of tert-butyl hydroperoxide into tert-butyl alcohol over Me-OMS-1s molecular sieves", J. Chem. Ind. Eng., 2015, vol. 66, pp. 3965-3970.

Hutson, "Phillips HF Alkylation Process for Alkylation of C3, C4, C5 Olefins", Handbook of Petroleum Refining Processes, R.A. Meyers., Ed.,.

Lin et al., "Decomposition of tert-butyl hydroperoxide into tert butyl alcohol and O2 catalyzed by bimessite-type manganese oxides: Kinetics and activity", Cat. Comm., 2014, vol. 49, pp. 6-9.

Liu et al., "Catalytic Partial Oxidation of Cyclohexane by Bimetallic Ag/Pd Nanoparticles on Magnesium Oxide", Chem. Eur. J.,.

Luo et al., "One-pot synthesis of MWW zeolite nanosheets using a rationally designed organic structure-directing agent", Chem. Sci., 2015, vol. 6, pp. 6320-6324.

O'Young, "Hydrothermal Synthesis of Manganese Oxides with Tunnel Structures", in Expanded Clays and Other Microporous Structures, vol. II, 333, M.L. Occelli, H.E. Robson Eds. Van Nostrand Reinhold, NY, 1992.

Shah, "UOP HF Alkylation Process", Handbook of Petroleum Refining Processes, R.A. Meyers, Ed., 1986, pp. XX-XX.

The International Search Report and Written Opinion of PCT/US2017/065954 dated Dec. 13, 2017.

The International Search Report and Written Opinion of PCT/US2017/065955 dated Dec. 13, 2017.

The International Search Report and Written Opinion of PCT/US2017/065958 dated Dec. 13, 2017.

The International Search Report and Written Opinion of PCT/US2017/065960 dated Dec. 13, 2017.

* cited by examiner

PRODUCTION OF ALKYLATE FROM LIGHT ALKANES

CROSS-REFERENCE TO RELATED APPLICATIONS

This application claims the benefit of U.S. Provisional Application No. 62/433,833, filed on Dec. 14, 2016, the entire contents of which are incorporated herein by reference.

FIELD

Systems and methods are provided for production of alkylate from an isoparaffin feed.

BACKGROUND

In conventional petroleum processes, alkylate is typically used to describe a product formed by an alkaylation process involving an isoparaffin-containing feed and an olefin-containing feed. Industrially, alkylation reactions often correspond to the reaction of a $C_2$ to $C_5$ olefin, normally 2-butene, with isobutane in the presence of an acidic catalyst to produce a so-called alkylate. This alkylate is a valuable blending component in the manufacture of gasoline due not only to its high octane rating but also to its sensitivity to octane-enhancing additives. Industrial isoparaffin-olefin alkylation processes have historically used hydrofluoric or sulfuric acid catalysts under relatively low temperature conditions. The sulfuric acid alkylation reaction is particularly sensitive to temperature, with low temperatures being favored to minimize the side reaction of olefin polymerization. Acid strength in these liquid acid catalyzed alkylation processes is typically maintained at 88 to 94 weight percent by the continuous addition of fresh acid and the continuous withdrawal of spent acid. The hydrofluoric acid process is less temperature sensitive and the acid is more easily recovered and purified. A general discussion of sulfuric acid alkylation can be found in a series of three articles by L. F. Albright et al., "Alkylation of Isobutane with $C_4$ Olefins", 27 *Ind. Eng. Chem. Res.*, 381-397, (1988). For a survey of hydrofluoric acid catalyzed alkylation, see 1 Handbook of Petroleum Refining Processes 23-28 (R. A. Meyers, ed., 1986). An overview of the entire technology can be found in "Chemistry, Catalysts and Processes of Isoparaffin-Olefin Alkylation—Actual Situation and Future Trends, Corma et al., *Catal. Rev.—Sci. Eng.* 35(4), 483-570 (1993).

Both sulfuric acid and hydrofluoric acid alkylation share inherent drawbacks including environmental and safety concerns, acid consumption, and sludge disposal. Research efforts have, therefore, been directed to developing alkylation catalysts which are equally as effective as, or more effective than, sulfuric or hydrofluoric acids but which avoid many of the problems associated with these two acids.

U.S. Pat. No. 3,644,565 discloses alkylation of a paraffin with an olefin in the presence of a catalyst comprising a Group VIII noble metal present on a crystalline aluminosilicate zeolite having pores of substantially uniform diameter from about 4 to 18 angstrom units and a silica to alumina ratio of 2.5 to 10, such as zeolite Y. The catalyst is pretreated with hydrogen to promote selectivity.

U.S. Pat. No. 4,384,161 describes a process of alkylating isoparaffins with olefins to provide alkylate using a large-pore zeolite catalyst capable of absorbing 2,2,4-trimethylpentane, for example, ZSM-4, ZSM-20, ZSM-3, ZSM-18, zeolite Beta, faujasite, mordenite, zeolite Y and the rare earth metal-containing forms thereof, and a Lewis acid such as boron trifluoride, antimony pentafluoride or aluminum trichloride. The addition of a Lewis acid is reported to increase the activity and selectivity of the zeolite, thereby effecting alkylation with high olefin space velocity and low isoparaffin/olefin ratio.

U.S. Pat. No. 5,304,698 describes a process for the catalytic alkylation of an olefin with an isoparaffin comprising contacting an olefin-containing feed with an isoparaffin-containing feed with a crystalline microporous material selected from the group consisting of MCM-22, MCM-36, and MCM-49 under alkylation conversion conditions of temperature at least equal to the critical temperature of the principal isoparaffin component of the feed and pressure at least equal to the critical pressure of the principal isoparaffin component of the feed.

An additional difficulty with alkylation processes can be related to the availability and/or cost of the feeds for forming alkylate. Light paraffin feeds, such as a feed containing isobutane, are generally considered low cost feeds. However, the corresponding olefin feed for forming alkylate can generally be of higher cost, particularly when the corresponding olefin feed corresponds to a $C_{3+}$ olefin feed, such as a feed of butene or isobutene, because these olefins are typically produced via dehydrogenation reaction which is a high temperature, thermodynamically limited process.

U.S. Pat. No. 5,243,084 describes a process for oxidation of isobutane to tertiary butyl hydroperoxide and tertiary butyl alcohol.

SUMMARY

In various aspects, a method for producing alkylate is provided. The method can include exposing an isoparaffin-containing feed to oxidation conditions in the presence of oxygen to form an oxidation effluent comprising tertiary alcohol. In some aspects, at least 0.5 wt % of the isoparaffins in the isoparaffin-containing feed can be converted under the oxidation conditions. Optionally, the tertiary alcohol can be tertiary butyl alcohol. At least a portion of the oxidation effluent can then be exposed to a solid acid catalyst under alkylation conditions to form an alkylation effluent. The at least a portion of the oxidation effluent can comprise a molar ratio of isoparaffin to tertiary alcohol of about 5:1 to about 200:1.

In some aspects, the isoparaffins in the isoparaffin-containing feed can correspond to $C_{4+}$ isoparaffins, $C_4$-$C_6$ isoparaffins, or isobutene. In such aspects, the isoparaffin-containing feed can comprise at least 80 wt % $C_{4+}$ isoparaffins, or at least 80 wt % $C_4$-$C_6$ isoparaffins, or at least 80 wt % isobutene, relative to a weight of the isoparaffin-containing feed (or at least 90 wt %, or at least 95 wt %, or at least 99 wt %).

In an aspect, the oxidation effluent can comprise a molar ratio of isoparaffin to tertiary alcohol of about 10:1 to about 100:1. In an aspect, the at least a portion of the oxidation effluent can comprise at least 1.0 mol % t-butyl alcohol.

In some aspects, the alkylation effluent can comprise a naphtha boiling range portion having an octane rating, as determined by (RON+MON)/2, of at least 85, or at least 90, or 85 to 100, or 90 to 100. Optionally, a portion of the alkylation effluent can be recycled as part of the isoparaffin-containing feed. In some aspects, the oxidation effluent can further comprise water, one or more oxygenates (such as methanol and/or acetone), or a combination thereof.

In some aspects, the solid acid catalyst can comprises a zeolite and/or a mixed metal oxide. For example, the solid acid catalyst can comprise a crystalline microporous material of the MWW framework type, such as MCM-49. More generally, a crystalline microporous material of the MWW framework type can optionally be selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and mixtures thereof. Optionally, an MWW framework type material can contain up to 10% by weight of impurities of other framework structures.

In some aspects, the solid acid catalyst can further comprise an inorganic oxide binder in an amount of 0-90 weight %, or 0-50 weight %, or 0-20 weight %, or 0-10 weight %, or 1-90 weight %, or 1-50 weight %, or 1-20 weight %, or 1-10 weight %. Optionally, the inorganic oxide binder can comprise alumina, or the inorganic oxide binder can be substantially free of amorphous alumina. Optionally, the inorganic oxide binder comprises silica.

In some aspects, the alkylation conditions can include a temperature of at least about 130° C., or at least about 170° C., or at least about 250° C.

In some aspects, the alkylation effluent can comprise a $C_8$ fraction comprising at least 50 wt % of 2,3,4, 2,3,3 and 2,2,4-trimethylpentane relative to a weight of the $C_8$ fraction, or at least 70 wt %.

In various aspects, a hydrocarbon product produced by alkylation of an isoparaffin feed is provided. The hydrocarbon product can include at least 60 mol % isobutane and 0.01 mol % to 0.5 mol % acetone on a dry basis. The hydrocarbon product can further include a $C_8$ fraction comprising at least 50 wt % of 2,3,4, 2,3,3 and 2,2,4-trimethylpentane relative to a weight of the $C_8$ fraction, or at least 70 wt %.

In various aspects, a system for producing alkylate from an isoparaffin feed is provided. The system can include an oxidation reactor comprising an isoparaffin feed inlet and an oxidation reactor outlet. The system can further include an alkylation reactor comprising an alkylation reactor inlet, an alkylation reactor outlet, and a solid acid catalyst, the alkylation reactor inlet being in fluid communication with the oxidation reactor outlet. Optionally, the solid acid catalyst can comprise a zeolite, a mixed metal oxide, a crystalline microporous material of the MWW framework type, or a combination thereof. Optionally, the alkylation reactor inlet optionally can be in direct fluid communication with the oxidation reactor outlet.

DETAILED DESCRIPTION

Overview

In various aspects, systems and methods are provided for forming alkylate from an isoparaffin-containing feed. Instead of using an olefin co-feed to form alkylate, olefins for the alkylation reaction can be generated from a portion of the isoparaffin-containing feed. This can be achieved, for example, by using selective oxidation to convert a portion of isoparaffins into alcohol, such as conversion of isobutane to t-butyl alcohol. The alcohol can then be converted to an alkene, such as conversion of t-butyl alcohol to isobutene, in the alkylation reaction environment. It has been unexpectedly discovered that a solid acid catalyst can facilitate conversion of tertiary alcohols to alkene under alkylation conditions. A solid acid catalyst can then facilitate alkylation of isoparaffin using the in-situ formed alkenes in the presence of the in-situ formed water. This conversion of alcohol to alkene, and then alkene alkylation of the isoparaffin, can occur in part due to the ability of a solid acid catalyst to tolerate water. A catalyst having an MWW framework is an example of a suitable solid acid catalyst.

Figure 1:
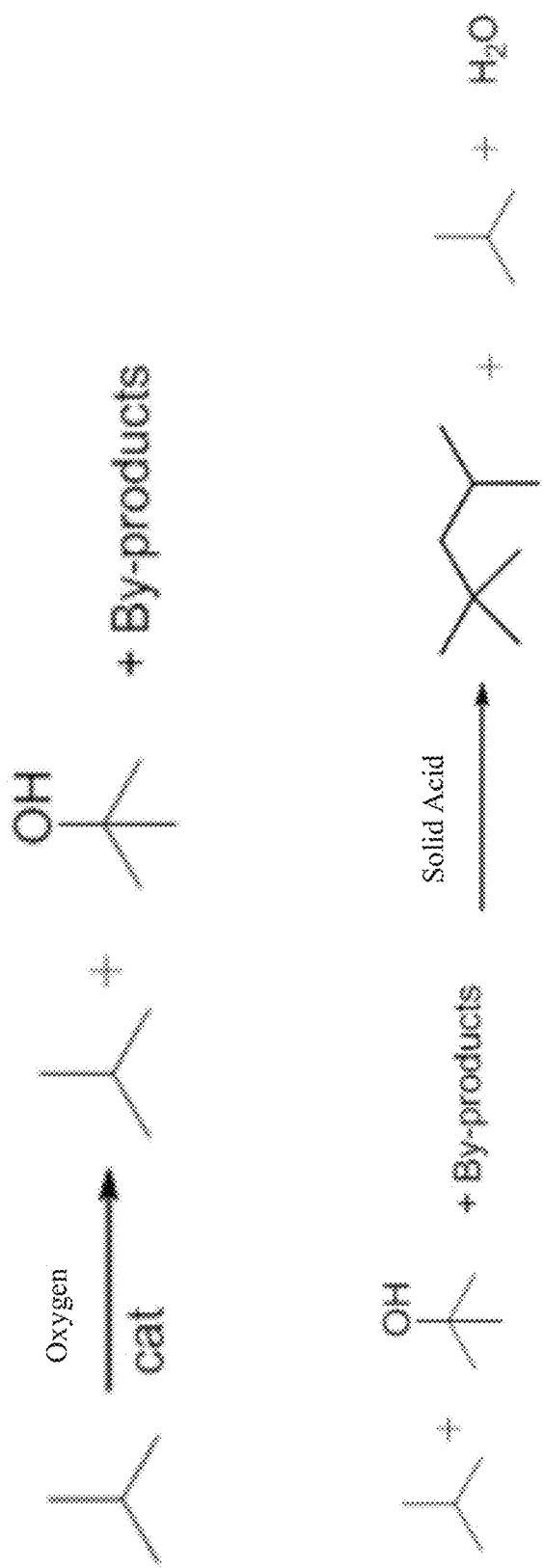
FIG. 1 show an example of a reaction scheme for forming alkylate from isoparaffins via oxidation of a portion of the isoparaffins to form alcohols.

FIG. 1 shows an example of the overall reaction scheme that can be used to form alkylate from an isoparaffin feed. In a first reactor and/or reaction stage, an isoparaffin feed (or a portion of such a feed) can be exposed to selective oxidation conditions. In FIG. 1, the isoparaffin feed is represented by isobutane. The selective oxidation conditions can result in only partial conversion of the feed, so that the resulting products include a substantial portion of unreacted isoparaffin. In addition to unreacted isoparaffin, the selective oxidation conditions can form t-butyl alcohol and various additional side products, such as water and acetone. This mixture from selective oxidation step has been found to be an effective feed, without separation, for produce an alkylation. In a second reactor and/or reaction stage, a mixture of unreacted isoparaffin and alcohol (and optionally at least a portion of the additional side products) can be exposed to a solid acid catalyst under controlled dehydration/alkylation conditions. Some examples of solid acid catalysts include zeolitic catalysts, such as catalysts having an MWW framework type. An MWW framework catalyst corresponds to a catalyst including a crystalline microporous material of the MWW framework type. The solid acid catalyst can convert the alcohol to alkene at substantially 100% conversion, and then alkylate the isoparaffin, resulting in the formation of alkylate, such as the 2,2,4-trimethyl pentane (isooctane) shown in FIG. 1. Because alkylation reactions are typically performed with an excess of isoparaffin to reduce or minimize olefin oligomerization reactions, the remaining unreacted isoparaffin from the alkylation reaction (and/or from the oxidation reaction) can be recycled for further passes through the reaction process train. The net result can be the upgrading of a low value isobutane stream to high octane blending component for gasoline.

A common method for characterizing the octane rating of a composition is to use an average of the Research Octane Number (RON) and the Motor Octane Number (MON) for a composition. This type of octane rating can be used to determine the likelihood of "knocking" behavior when operating a conventional spark ignition engine. In this discussion, octane rating is defined as (RON+MON)/2, where RON is research octane number and MON is motor octane number. Although various methods are available for determining RON and MON, in the claims below, references to Research Octane Number (RON) correspond to RON determined according to ASTM D2699, while references to Motor Octane Number (MON) correspond to MON determined according to ASTM D2700.

In this discussion, the naphtha boiling range is defined as about 50° F. (~10° C., roughly corresponding to the lowest boiling point of a pentane isomer) to 350° F. (~177° C.). It is noted that due to practical consideration during fractionation (or other boiling point based separation) of hydrocarbon-like fractions, a fuel fraction formed according to the methods described herein may have a T5 or a T95 distillation point corresponding to the above values, as opposed to having initial/final boiling points corresponding to the above values. Compounds ($C_{4-}$) with a boiling point below the naphtha boiling range can be referred to as light ends. Optionally, a naphtha boiling range fuel composition can have a higher T5 distillation point, such as a T5 distillation point of at least about 15° C., or at least about 20° C., or at least about 30° C. In particular, a naphtha boiling range fuel composition can have a T5 to T95 distillation point range corresponding to a T5 of at least about 10° C. and a T95 of about 177° C. or less; or a T5 of at least about 15° C. and a T95 of about 177° C. or less. In the claims below, ASTM D86 should be used for determining boiling points (including fractional weight boiling points). Compounds with boiling points above 177° C. can correspond to distillate fuel boiling range compounds.

Solid acid catalysts can generally refer to solid materials that can provide acidic sites for catalysis of reactions. Some examples of solid acid catalysts can include various types of zeolites and/or molecular sieves. For example, in zeolitic structures that include silicon and aluminum in the framework, the aluminum atoms can potentially serve as acidic catalysis sites. Suitable zeolitic materials for use as solid acid catalysts can include ZSM-4, ZSM-20, ZSM-3, ZSM-18, zeolite Beta, faujasite, mordenite, zeolite Y and the rare earth metal-containing forms thereof. More generally, crystalline materials having a porous framework structure built from tetrahedra atoms connected by bridging oxygen atoms can potentially be suitable solid acid catalysts. This can include aluminosilicates having a zeolitic framework as well as crystalline structures containing oxides of heteroatoms different from silicon and aluminum. Such heteroatoms can include any heteroatom generally known to be suitable for inclusion in a zeolitic framework, such as gallium, boron, germanium, phosphorus, zinc, and/or other transition metals that can substitute for silicon and/or aluminum in a zeolitic framework Still other examples of solid acid catalysts can include mixed metal oxides. Examples of suitable mixed metal oxides can include mixed metal oxides based on oxides of Fe/W/Zr, W/Zr, Ce/W/Zr, Cu/W/Zr, and/or Mn/W/Zr.

As used herein, the term "crystalline microporous material of the MWW framework type" includes one or more of: a) Molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, which is incorporated by reference with respect to definitions for unit cells, building blocks, and crystal structures); b) Molecular sieves made from a common second degree building block, being a 2-dimensional tiling of such MWW framework topology unit cells, forming a monolayer of one unit cell thickness, preferably one c-unit cell thickness; c) Molecular sieves made from common second degree building blocks, being layers of one or more than one unit cell thickness, wherein the layer of more than one unit cell thickness is made from stacking, packing, or binding at least two monolayers of MWW framework topology unit cells. The stacking of such second degree building blocks can be in a regular fashion, an irregular fashion, a random fashion, or any combination thereof; and d) molecular sieves made by any regular or random 2-dimensional or 3-dimensional combination of unit cells having the MWW framework topology.

Crystalline microporous materials of the MWW framework type include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Examples of crystalline microporous materials of the MWW framework type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), UZM-8HS (described in U.S. Pat. No. 7,713,513), UZM-37 (described in U.S. Pat. No. 7,982,084); EMM-10 (described in U.S. Pat. No. 7,842,277), EMM-12 (described in U.S. Pat. No. 8,704,025), EMM-13 (described in U.S. Pat. No. 8,704,023), MIT-1 (described by Luo et al in Chem. Sci., 2015, 6, 6320-6324), and mixtures thereof, with MCM-49 generally being preferred.

In some embodiments, the crystalline microporous material of the MWW framework type employed herein may be an aluminosilicate material having a silica to alumina molar ratio of at least 10, such as at least 10 to less than 50.

In some embodiments, the crystalline microporous material of the MWW framework type employed herein may be contaminated with other crystalline materials, such as ferrierite or quartz. These contaminants may be present in quantities of less than about 10% by weight, normally less than aboutt 5% by weight.

The above molecular sieves may be formed into extrudates with or without another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia, or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide binder may vary widely. For example, the amount of binder employed may be as little as 0 wt %, or alternatively at least 1 wt %, or at least 5 wt %, or at least 10 wt %, whereas in other embodiments the catalyst may include up to 90 wt %, for example up 80 wt %, such as up to 70 wt %, for example up to 60 wt %, such as up to 50 wt % of a binder material.

In an aspect, a solid acid catalyst can be substantially free of any binder containing amorphous alumina. As used herein, the term "substantially free of any binder containing amorphous alumina" means that the solid acid catalyst used herein contains less than 5 wt %, such as less than 1 wt %, and preferably no measurable amount, of amorphous alumina as a binder. Surprisingly, it is found that when the solid acid catalyst is substantially free of any binder containing amorphous alumina, the activity of the catalyst for isoparaffin-olefin alkylation can be significantly increased, for example by at least 50%, such as at least 75%, even at least 100% as compared with the activity of an identical catalyst but with an amorphous alumina binder.

Oxidation of Isobutane to Form Mixed Feed of Isobutane and t-Butyl Alcohol

Oxidation of isobutane for formation of t-butyl hydroperoxide is a known industrial process. While this oxidation process is often employed for production of peroxides, the process also generates t-butyl alcohol. The amount of alcohol production can vary depending on the conditions and the reaction configuration. For example, U.S. Pat. No. 5,243,084 describes systems and methods for producing t-butyl alcohol as a product from oxidation of isobutane.

In various aspects, oxidation of isobutane (and/or other $C_5$-$C_6$ isoparaffins) to form t-butyl alcohol (and/or other tertiary $C_5$-$C_6$ alcohols) can be performed by any convenient known oxidation method. The isoparaffin-containing feed can correspond to a feed including isobutane, $C_{4+}$ isoparaffins, $C_{5+}$ isoparaffins, $C_4$-$C_5$ isoparaffins, or $C_4$-$C_6$ isoparaffins. In some aspects, the isoparaffin-containing feed can contain at least 80 wt % of isoparaffins (and up to 100 wt %), or at least 90 wt %, or at least 95 wt %, or at least 99 wt %, such as a feed that substantially contains isoparaffins (i.e., 99.5 wt % or higher). In some aspects, the isoparaffin-containing feed can correspond to an isobutane-containing feed that contains at least 80 wt % of isobutane (and up to 100 wt %), or at least 90 wt %, or at least 95 wt %, or at least 99 wt %, such as a feed that substantially contains isobutane (i.e., 99.5 wt % or higher). In various aspects, other components present in the isoparaffin-containing feed (such as an isobutane-containing feed) can include n-paraffins, cycloparaffins, and/or less than about 2 wt % of compounds typically present due to the nature of a process that generated the isoparaffin feed.

As an example, isobutane can be reacted with oxygen in a reactor to produce a mixture of t-butyl hydroperoxide along with t-butyl alcohol. The isobutane oxidation reaction conditions in the oxidation reactor can include, for example, a reaction temperature of about 100° C. to about 200° C., a pressure of about 200 psig (~1.4 MPag) to about 500 psig (~3.4 MPag), and a residence time in the oxidation zone of about 1 hour to about 15 hours. Oxygen can be used as the oxidant, although minor amounts of nitrogen and/or other inert gases can also be present.

The above reaction conditions can generate a weight ratio of t-butyl alcohol to t-butyl hydroperoxide in the liquid phase of about 0.8. Due to the higher vapor pressure of t-butyl alcohol, withdrawing the vapor above the reaction zone can result in a gas phase product with a weight ratio of t-butyl alcohol to t-butyl hydroperoxide of roughly 1.0. This can be facilitated, for example, by operating the oxidation reactor to maintain the reaction mixture at or near the boiling point. The withdrawn vapor can also include, for example, unreacted isobutane and other additional reaction side products. These additional reaction products can include, for example, water and oxygenate impurities, such as methanol and acetone. Depending on the nature of the fractionation, the ratio of t-butyl alcohol to t-butyl hydroperoxide can be further increased. In some aspects, a fraction enriched in t-butyl hydroperoxide can be returned to the oxidation reactor. For a fraction containing t-butyl alcohol, the fraction can optionally be exposed to elevated temperatures of about 100° C. to about 200° C. for additional time to allow for further decomposition of t-butyl hydroperoxide to t-butyl alcohol. Without being bound by any particular theory, it is believed that forming alcohols from isoparaffins by oxidation as described herein can provide a method for alcohol formation under lower severity conditions in comparison with processes such as high temperature reforming. This can allow the conditions for formation of alcohol to be more similar to the eventual conditions for alkylate formation. Additionally or alternately, it is believed that the selectivity of alcohol formation can be improved relative to a high temperature reforming process.

For subsequent alkylation, a desirable effluent fraction from an oxidation process can have a molar ratio and/or volume ratio of isobutane to t-butyl alcohol of about 5:1 to about 200:1, or about 5:1 to about 100:1, or about 10:1 to about 100:1, or about 10:1 to about 40:1. This can correspond to, for example, conversion of at least about 0.5 wt % of the isobutane under the oxidation conditions, or at least about 1.0 wt %. In some aspects, a fraction generated by the isobutane oxidation reaction may have a suitable ratio of t-butyl alcohol to isobutane. In other aspects, a product fraction from the isobutane oxidation reaction can be blended with additional isobutane to form a feed for alkylation.

It is noted that other isoparaffins can potentially be oxidized to generate tertiary alcohols. For example, an isopentane or isohexane feed could be oxidized to generated tertiary alcohols. This could be useful, for example, if an available source of isoparaffins includes a mixture of $C_{4+}$ isoparaffins. While use of higher carbon number isoparaffins could lead to formation of compounds during alkylation that are above the traditional naphtha boiling range for gasoline formation, such heavier compounds can be readily separated by boiling point separation and used as part of a distillate fuel fraction.

Another potential difficulty with $C_{5+}$ isoparaffins is that such isoparaffins contain multiple types of carbon sites. Isobutane corresponds to an isoparaffin with three primary (i.e., terminal) carbons and one tertiary carbon. When isobutane is oxidized, the selectivity for forming t-butyl alcohol is high, as the primary carbons have only a limited ability to stabilize the reaction intermediates that could allow for formation of an alcohol. Additionally, once t-butyl alcohol is formed, little or no transfer of the alcohol from the tertiary carbon to a primary carbon would be expected. By contrast, an isopentane (such as 2-methylbutane) includes 3 primary carbons, a tertiary carbon, and a secondary carbon. While the tertiary carbon is the most favorable location for formation of an alcohol, the secondary carbon can also be a suitable location. As a result, oxidation of a $C_{5+}$ isoparaffin can typically result in formation of a mixture of alcohols. Additionally, the presence of multiple non-primary carbons can also facilitate migration of the alcohol group after formation and/or migration of the double bond in the resulting in-situ olefin. As a result, using alcohols formed from $C_{5+}$ paraffins can tend to lead to production of a larger mixture of alkylate products, as opposed to the relatively high selectivity for formation of tri-methylpentanes that is exhibited when isobutane is used as the feed for oxidation. Because tri-methylpentanes can have a relatively high octane value, the formation of a wider variety of products when using $C_{5+}$ isoparaffins can tend to reduce the octane value of the resulting alkylate.

Before being sent to the oxidation reactor and/or the alkylation reactor, the isoparaffin feed and/or the oxidation product fraction containing the tertiary alcohol may be treated to remove catalyst poisons e.g., using guard beds with specific absorbents for reducing the level of S, N, and/or organic acids to values which do not affect catalyst stability activity and selectivity. It is noted that the alkylation process described herein can be conducted in any known reactor, including reactors which allow for continuous or semi-continuous catalyst regeneration, such as fluidized and moving bed reactors, as well as swing bed reactor systems where multiple reactors are oscillated between on-stream mode and regeneration mode. Surprisingly, however, it is found that catalysts employing MWW framework type molecular sieves show unusual stability when used in isoparaffin-olefin alkylation. Thus, MWW-containing alkylation catalysts can be suitable for use in simple fixed bed reactors (including trickle-bed reactors), without swing bed capability. In such cases, cycle lengths (on-stream times between successive catalyst regenerations) in excess of 150 days may be obtained.

Alkylation of Isobutane with t-Butyl Alcohol

In various aspects, a mixed feed of isobutane and t-butyl alcohol can be formed based on generation of t-butyl alcohol as described above. In some aspects, the feed can include isobutane and t-butyl alcohol in a molar ratio and/or volume ratio of about 10:1 to about 40:1. Optionally, the feed can also include other oxygenates, such as methanol and/or acetone formed as additional products during oxidation. More generally, the molar ratio and/or volume ratio of isoparaffin to tertiary alcohol in the reactor feed can be from about 2:1 to about 100:1, or about 10:1 to about 75:1, or about 10:1 to about 40:1, so as to produce a high quality alkylate product at industrially useful yields. Optionally, one or more additional oxygenate products generated during oxidation, such as methanol and/or acetone, may be included as part of the oxidation product fraction containing the t-butyl alcohol. In some aspects, the molar ratio and/or volume ratio of t-butyl alcohol to acetone in an oxidation product fraction (and/or the feed to alkylation) can be about 8:1 to about 200:1, or about 8:1 to about 100:1, or about 10:1 to about 150:1. In some aspects, the molar ratio and/or volume ratio of t-butyl alcohol to methanol in an oxidation product fraction (and/or the feed to alkylation) can be about 8:1 to about 200:1, or about 8:1 to about 100:1, or about 10:1 to about 150:1. At typical alkylation temperatures, the volume ratio of components in an alkylation feed and/or in an alkylation effluent can be similar to the molar ratio.

In aspects where additional isobutane is added to the oxidation product fraction that contains t-butyl alcohol (and/or another tertiary alcohol) in order to achieve a desired volume ratio in the feed, the olefin-containing feedstock and the isoparaffin-containing feedstock may be mixed prior to being fed to the alkylation reaction zone or may be supplied separately to the reaction zone.

During the alkylation process, the t-butyl alcohol (and/or other tertiary alcohol) can be substantially quantitatively converted to olefin under the alkylation conditions in the presence of a solid acid catalyst. The resulting olefins can then react to form alkylate under the alkylation conditions in the presence of the solid acid catalyst.

The alkylation process can be conducted at temperatures from about 250° F. to about 700° F. (121° C. to 371° C.), such as from about 300° F. to about 600° F. (149° C. to 316° C.). Operating temperatures typically exceed the critical temperature of the principal component in the feed. The term "principal component" as used herein is defined as the component of highest concentration in the feedstock. For example, isobutane is the principal component in a feedstock consisting of isobutane and t-butyl alcohol in an isobutane:t-butyl alcohol molar ratio of 40:1. In some aspects, the alkylation temperature can be at least about 130° C., or at least about 170° C., or at least about 200° C., or at least about 250° C.

Operating pressure may similarly be controlled to maintain the principal component of the feed in the supercritical state, and can suitably be from about 300 to about 1500 psig (~2.1 MPag to ~10.3 MPag), such as about 400 psig (~2.8 MPag) to about 1000 psig (6.9 MPag). In some aspects, the operating temperature and/or pressure can remain above the critical value for the principal feed component during the entire process run, including the first contact between fresh catalyst and fresh feed.

Hydrocarbon flow through the alkylation reaction zone containing the catalyst is typically controlled to provide an olefin liquid hourly space velocity (LHSV) sufficient to convert about 99 percent by weight of the fresh olefin to alkylate product. In some embodiments, olefin LHSV values fall within the range of about 0.01 to about 10 hr$^{-1}$. Because the conversion of tertiary alcohol to olefin in the reactor is substantially quantitative, the olefin LHSV and the tertiary alcohol LHSV can be roughly the same.

The product composition of the isoparaffin-olefin alkylation reaction described herein can be dependent on the reaction conditions and the composition of the tertiary alcohol and isoparaffin feedstock(s). In any event, the product is a complex mixture of hydrocarbons, since alkylation of the feed isoparaffin by the in-situ produced olefin is accompanied by a variety of competing reactions including cracking, olefin oligomerization and further alkylation of the alkylate product by the feed olefin. It is noted that when using an isobutane feed to form t-butyl alcohol and then alkylation is performed using a feed of isobutane and t-butyl alcohol, the resulting products can include a $C_8$ fraction that can comprise at least 50 wt %, such as at least 70 wt %, of 2,3,4, 2,3,3 and 2,2,4-trimethylpentane relative to the weight of the $C_8$ fraction. This can correspond to an alkylate product having a higher octane value than would be obtained by a comparable process where isobutane and isobutene feeds are reacted using sulfuric acid as the catalyst. In some aspects, a naphtha boiling range portion of the alkylation effluent can have an octane rating, as determined based on (RON+MON)/2, of at least 85, or at least 87, or at least 90, or at least 92, or at least 94, or at least 96. In particular, in some aspects the naphtha boiling range portion of the alkylation effluent can have an octane rating of about 85 to about 100, or about 90 to about 100, or about 92 to about 98, or about 92 to about 100. Additionally, in aspects where oxygenate impurities are present in the initial feed to the alkylation reaction, a portion of those impurities can be present in the alkylation effluent. For example, acetone generated during selective oxidation of isobutane may not be fully converted under alkylation conditions. In aspects where acetone from a selective oxidation process is included as part of the feed to the alkylation reactor, unconverted acetone can correspond to 0.01 mol % to 0.5 mol % of the alkylation effluent on a dry basis, or 0.05 mol % to 0.5 mol %. Dry basis refers to the hydrocarbon portion of the alkylation effluent, which excludes any water present in the alkylation effluent.

The product of the isoparaffin-olefin alkylation reaction can be, for example, conveniently fed to a separation system, such as a distillation train, to recover the $C_{9-}$ fraction for use as a gasoline octane enhancer. Depending on alkylate demand, part of all of the remaining $C_{10+}$ fraction can be recovered for use as a distillate blending stock or can be recycled to the alkylation reactor to generate more alkylate. In particular, it is found that MWW type molecular sieves are effective to crack the $C_{10+}$ fraction to produce light olefins and paraffins which can react to generate additional alkylate product and thereby increase overall alkylate yield.

Example Configuration

Figure 2:
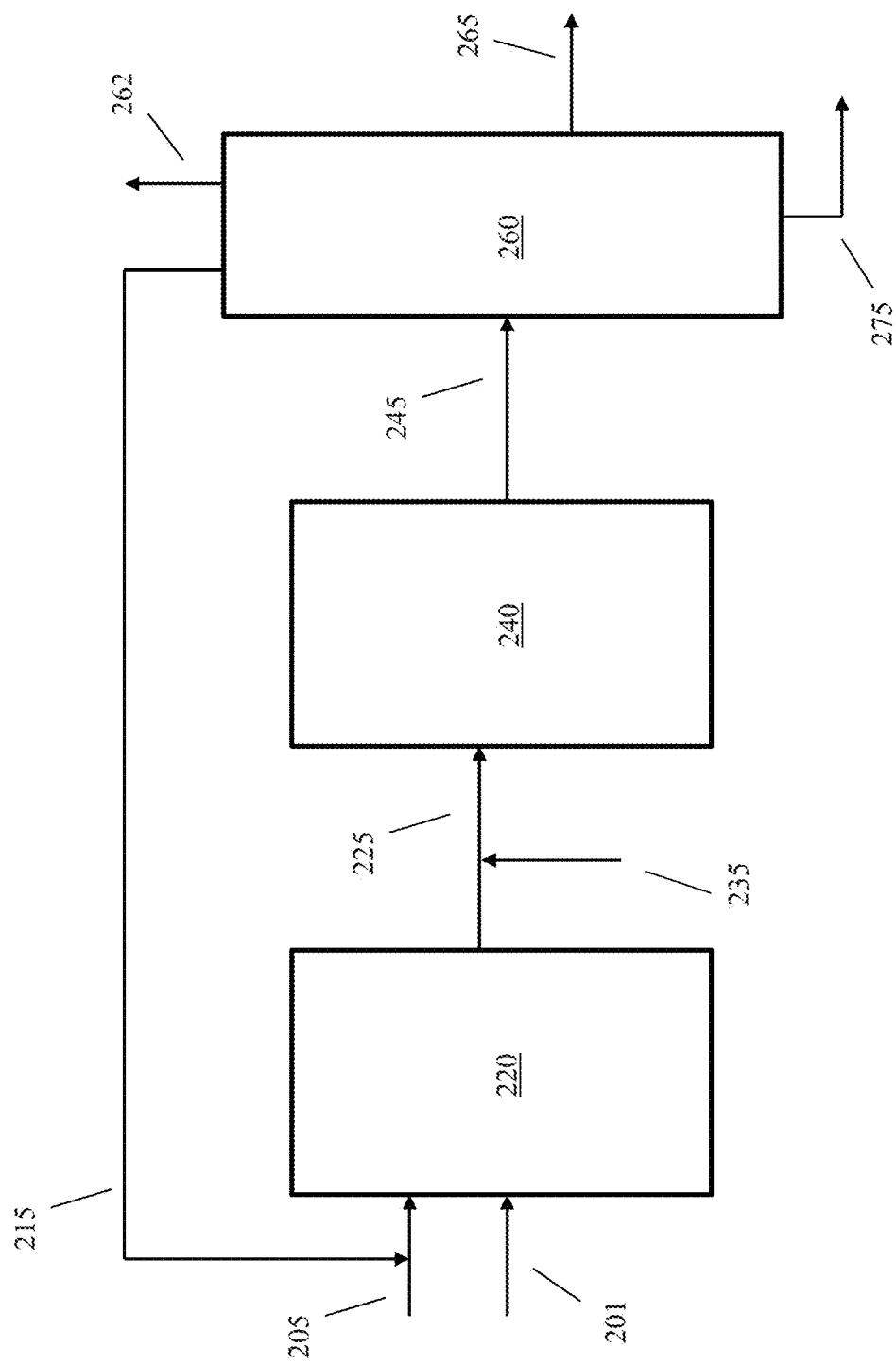
FIG. 2 schematically shows an example of a process configuration for producing alkylate from isoparaffins.

FIG. 2 shows an example of a reactor configuration for converting isoparaffins (such as isobutane) to alkylate. In FIG. 2, a feed 205 including isoparaffins (such as isobutane) can be introduced into an oxidation reactor 220 via a reactor inlet. The feed 205 can also include a recycle stream 215 of isobutane that did not react during the prior pass through the reactor configuration. An oxygen-containing stream 201, such as air, can also be introduced via an oxidant inlet. The isoparaffin and oxygen are reacted in the oxidation reactor 220 to form an oxidation effluent stream 225 that includes the isoparaffin and alcohol formed from the isoparaffin. The oxidation effluent stream 225 can exit from a reactor outlet. Optionally, an additional stream 235 of isoparaffin can be added to the oxidation effluent stream 225 to achieve a desired ratio of isoparaffin to alcohol in oxdiation effluent stream 225. Optionally, oxidation effluent stream 225 can include additional oxygenates and/or other products formed during oxidation, such as methanol and/or acetone. The effluent stream 225 (or at least a portion thereof) can then be introduced into alkylation reactor 240 via a reactor inlet. Alkylation reactor 240 can include a solid acid catalyst (such as an MWW framework catalyst, for example MCM-49). The effluent stream 225 can be exposed to the catalyst in alkylation reactor 240 under alkylation conditions to generate an alkylation effluent 245 that exits via a reactor outlet. The alkylation effluent 245 can then be fractionated in a fractionator 260 (or other separation stage) to generate a variety of products. Optionally, a separation stage can correspond to a plurality of separators to produce desired fractions from the alkylation effluent 245. In the example shown in FIG. 2, the alkylation effluent 245 is separated to form a water product 262, an alkylate product 265, a distillate fuels boiling range product (177° C.+) 275, and an unreacted isoparaffin stream 215 that can optionally but preferably be recycled for use as part of isoparaffin feed 205. Optionally, other side products in the alkylation effluent that boil below the naphtha boiling range can also be separated out (not shown).

In the example configuration shown in FIG. 2, the outlet of the oxidation reactor 220 is shown as being in direct fluid communication with the inlet of the alkylation reactor 240. Direct fluid communication refers to fluid communication without passing through intervening reactor, separator, or other processing element that alters the composition of the effluent from the oxidation reactor 240. Fluid communication between reaction system elements that involves passing through one (or more) intervening processing elements can be referred to as indirect fluid communication.

Example 1

Preparation of 80 wt % MCM-49/20 wt % Alumina Catalyst 80 parts MCM-49 zeolite crystals were combined with 20 parts pseudoboehmite alumina, on a calcined dry weight basis. The MCM-49 and pseudoboehmite alumina dry powder were placed in a muller or a mixer and mixed for about 10 to 30 minutes. Sufficient water and 0.05% polyvinyl alcohol were added to the MCM-49 and alumina during the mixing process to produce an extrudable paste. The extrudable paste was formed into a 1/20 inch quadralobe extrudate using an extruder. After extrusion, the 1/20th inch quadralobe extrudate was dried at a temperature ranging from 250° F. to 325° F. (121° C. to 163° C.). After drying, the dried extrudate was heated to 1000° F. (538° C.) under flowing nitrogen. The extrudate was then cooled to ambient temperature and humidified with saturated air or steam.

After humidification, the extrudate was ion exchanged with 0.5 to 1 N ammonium nitrate solution. The ammonium nitrate solution ion exchange was repeated. The ammonium nitrate exchanged extrudate was then washed with deionized water to remove residual nitrate prior to calcination in air. After washing the wet extrudate was dried. The exchanged and dried extrudate was then calcined in a nitrogen/air mixture to a temperature 1000° F. (538° C.).

Example 2

Procedure for Alkylation

The reactor used in these experiments comprised a stainless steel tube having an internal diameter of 3/8 inches (~0.95 cm), a length of 20.5 inches (~52 cm) and a wall thickness of 0.035 inches (~0.089 cm). A piece of stainless steel tubing 8¾ inches (~22.2 cm) long×3/8 inches (~0.95 cm) external diameter and a piece of ¼ inch (~0.64 cm) tubing of similar length were positioned in the bottom of the reactor (one inside of the other) as a spacer to position and support the catalyst in the isothermal zone of the furnace. A ¼ inch (~0.64 cm) plug of glass wool was placed at the top of the spacer to keep the catalyst in place. A 1/8 inch (~0.32 cm) stainless steel thermo-well was placed in the catalyst bed, long enough to monitor temperature throughout the catalyst bed using a movable thermocouple. The catalyst was loaded with a spacer at the bottom to keep the catalyst bed in the center of the furnace's isothermal zone.

The catalyst was then loaded into the reactor from the top. The catalyst bed contained about 4.0 g of the MCM-49 catalyst of Example 1 sized to 14-25 mesh (700 to 1400 micron) and was 10 cm in length. A ¼ inch (~0.32 cm) plug of glass wool was placed at the top of the catalyst bed to separate quartz chips from the catalyst. The remaining void space at the top of the reactor was filled with quartz chips of similar size to the catalyst or larger (such as up to 14 mesh). The reactor was installed in the furnace with the catalyst bed in the middle of the furnace at the pre-marked isothermal zone. The reactor was then pressure and leak tested at 800 psig (~5.5 MPag).

A 500 cc ISCO syringe pump was used to introduce the feed to the reactor. A Grove "Mity Mite" back pressure controller was used to control the reactor pressure at about 750 psig (~5.2 MPag). On-line GC analyses were taken to verify feed and the product composition. The feed (chemical grade isobutane and TBA+ by-products were used) was then pumped through the catalyst bed with the catalyst bed held at 150° C. The products exiting the reactor flowed through heated lines routed to GC then to three cold (5-7° C.) collection pots in series. The non-condensable gas products were routed through a gas pump for analyzing the gas effluent. Material balances were taken at 24 hr intervals. Samples were taken for analysis. The material balance and the gas samples were taken at the same time while an on-line GC analysis was conducted for doing material balance.

Example 3

Examples of Alkylation Processes

The system and procedures of Example 2 (including the catalyst of Example 1) were used to perform alkylation on various feeds. It is believed that molar ratios for Feeds A, B, C, D, and E would be similar to the volume ratios reported in this example.

A first feed (Feed A) corresponded to a 40:1 (vol/vol) mixture of isobutane and isobutene. The alkylation reaction for Feed A was conducted for 8 days at a temperature of about 150° C. and an initial LHSV of about 5 $hr^{-1}$.

A group of feeds (Feeds B, C, and D) corresponded to various volume ratios of isobutane and t-butyl alcohol (TBA). Feed B corresponded to a 20:1 (vol/vol) mixture of isobutane and TBA. Feed C corresponded to a 40:1 (vol/vol) mixture of isobutane and TBA. Feed D corresponded to a 80:1 (vol/vol) mixture of isobutane and TBA. The alkylation reactions for Feeds B, C, and D were conducted for 8 days at temperatures of about 150° C. or about 170° C. and an initial LHSV of about 2.5 $hr^{-1}$.

A final feed (Feed E) corresponded to a 40:1 (vol/vol) mixture of isobutane and a mixture of TBA with acetone and methanol. The mixture of TBA, acetone, and methanol had a volume ratio of 0.88 TBA, 0.08 acetone, and 0.04 methanol. The alkylation reaction for Feed E was conducted for 8 days at temperatures of about 150° C. or about 200° C. and an initial LHSV of about 2.5 $hr^{-1}$.

Figure 3:
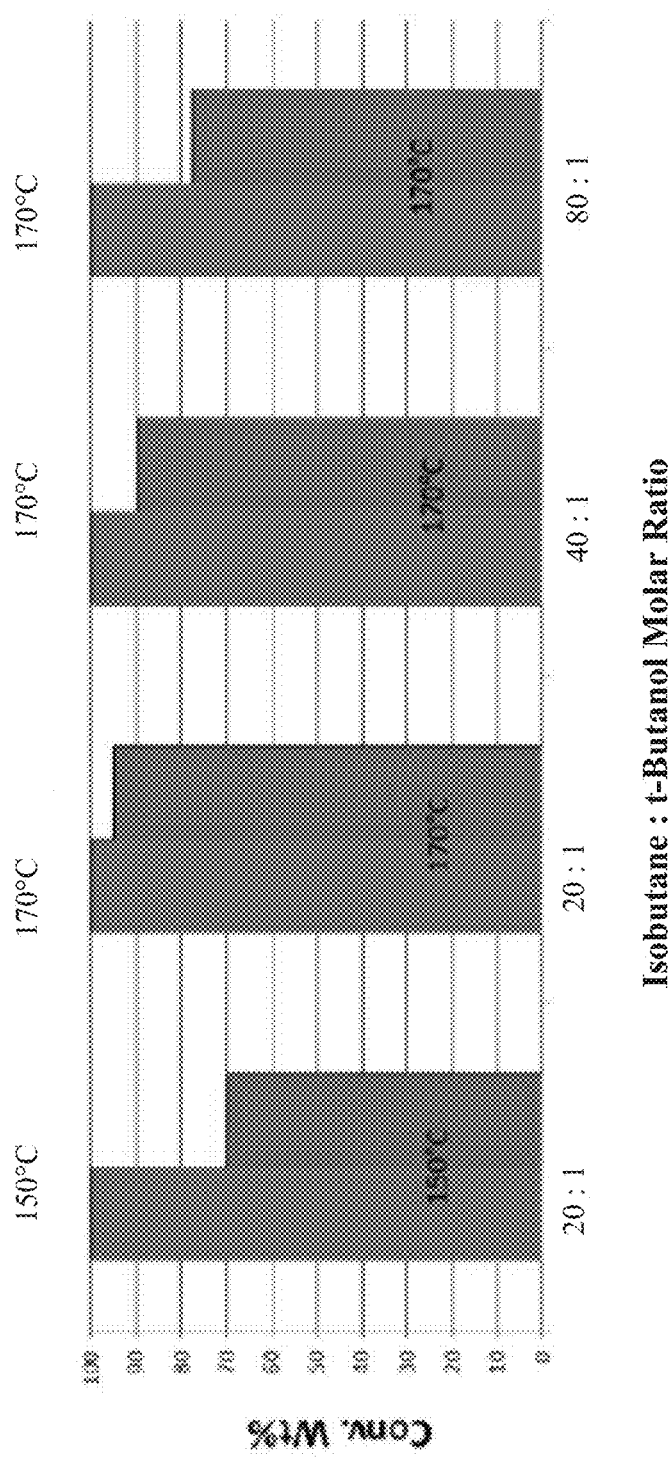
FIG. 3 shows results from performing alkylation using various mixtures of isobutane and t-butanol.

FIG. 3 shows results from processing Feeds B, C, and D at temperatures of 150° C. (Feed B) or 170° C. (Feeds B, C, and D) under the alkylation conditions in Example 2. In FIG. 3, the left bar in each pair of bars corresponds to the amount of conversion for TBA, while the right bar in each pair of bars corresponds to the amount of conversion of isobutene. As shown in FIG. 3, substantially all TBA in the reactor is converted at each of the conditions. It is believed that substantially all of the converted TBA results in formation of isobutene. Based on the results shown in FIG. 3, it appears that MWW framework catalysts such as MCM-49 are suitable for substantially complete in-situ conversion of TBA to isobutene under alkylation reaction conditions. More generally, solid acid catalysts (such as MWW framework catalysts) are believed to be suitable for conversion of TBA into isobutene, as well as potentially suitable for conversion of other tertiary alcohols to iso-olefins.

With regard to isobutene, conversion of isobutene can be due to alkylation or due to conversion via another competing reaction. As shown in FIG. 3, increasing the alkylation temperature to 170° C. increases the amount of TBA conversion. FIG. 3 also appears to show that reducing the relative ratio of isobutane to TBA in the feed resulted in greater conversion of the isobutene generated in the reaction environment. At both a 20:1 and 40:1 volume ratio of isobutane to TBA, the MCM-49 provided at least 90 wt % conversion of the in-situ generated isobutene. This demonstrates that MWW framework catalysts can be suitable for performing both in-situ generation of isobutene (and/or other iso-olefins) while also remaining suitable for providing high rates of olefin conversion under alkylation conditions. More generally, it is believed that other solid acid catalysts can be suitable for olefin conversion under alkylation conditions.

Figure 4:
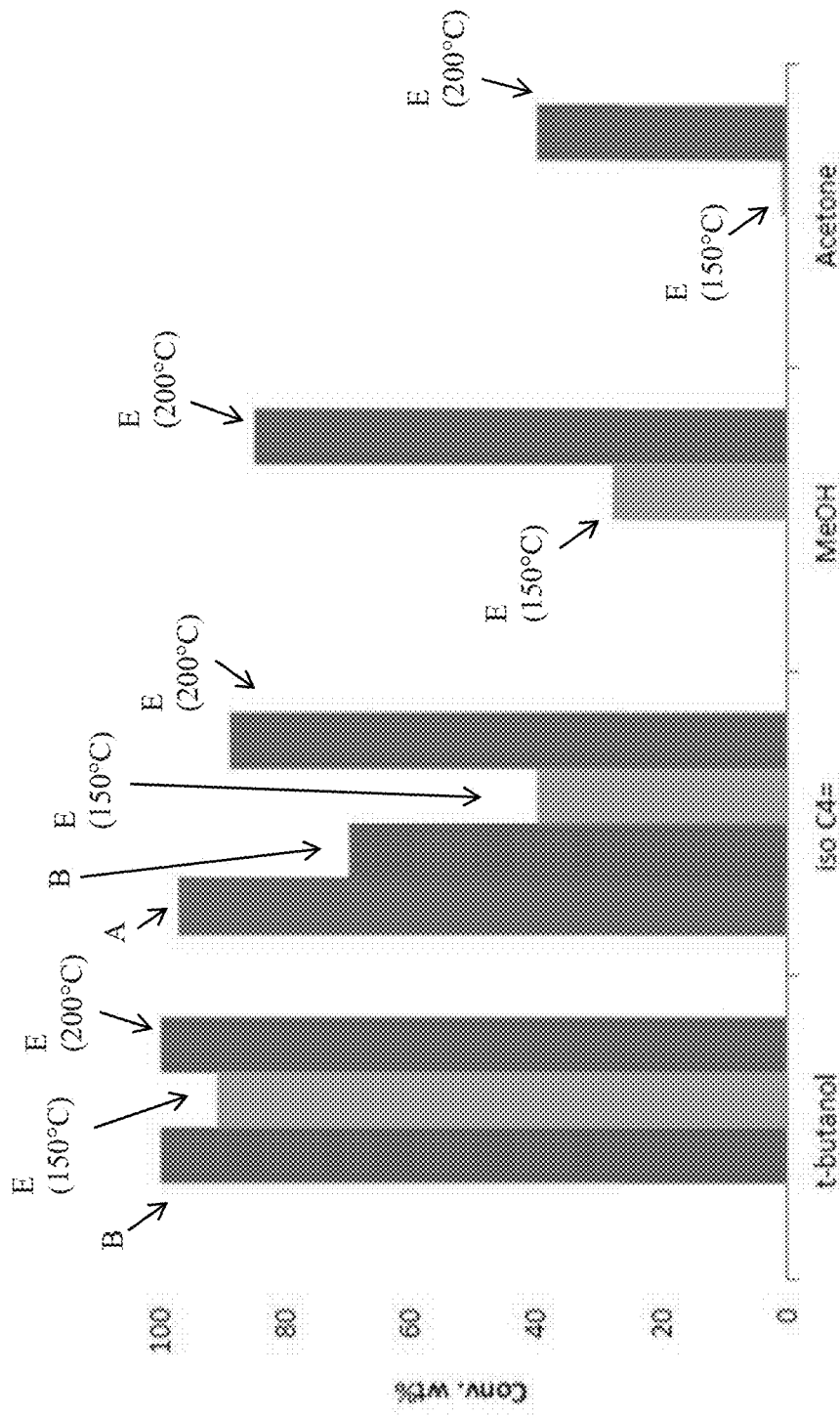
FIG. 4 shows results from performing alkylation using various feeds.

FIG. 4 shows results from processing Feed A (150° C.), Feed B (150° C.), and Feed E (150° C., 200° C.) under the alkylation conditions in Example 2. In FIG. 4, the conversion of various potential feed and/or intermediate components is shown. For each bar, the corresponding "Feed" is indicated. The first series of bars corresponds to the amount of TBA conversion during the reaction. It is noted that no bar for Feed A is included, since Feed A does not contain TBA. The second series of bars corresponds to the amount of isobutene converted. The third series of bars correspond to conversion of methanol, while the fourth series of bars correspond to acetone conversion. These components are only present in Feed E.

With regard to conversion of TBA, FIG. 4 shows that less than all of the TBA is converted at 150° C. when additional oxygenate components (methanol, acetone) are present in the feed to the alkylation reaction. Increasing the reaction temperature, such as to 200° C., allows for substantially complete conversion of TBA in the presence of such additional oxygenates.

The increase in reaction temperature to 200° C. also appears to allow for increased conversion of isobutene in the presence of additional oxygenates. Although the presence of additional oxygenates reduces the conversion of isobutene at 150° C. relative to a feed containing only TBA, the increase in reaction temperature to 200° C. can allow conversion of isobutene to be greater than 80 wt % in the presence of additional oxygenates. This is similar to the conversion percentage for isobutene in Feed A at 150° C.

Increasing the temperature to 200° C. also appears to allow for increased conversion of additional oxygenates present in a feed. As shown in FIG. 4, the amount of conversion of methanol at 150° C. is less than 30 wt %, while little or no conversion of acetone is observed. Increasing the temperature to 200° C. allows for conversion of more than 80 wt % of the methanol in the feed, while acetone conversion is increased to roughly 40 wt %.

Without being bound by any particular theory, the results in FIG. 4 appear to show that the presence of additional oxygenates in the alkylation feed can lead to reduced alkylation activity. It is believed that the presence of water in the alkylation environment can result in a similar lowering of alkylation activity. However, increasing the alkylation temperature can overcome this reduced activity and allow for production of alkylate with similar octane rating to alkylate formed by conventional methods.

Figure 5:
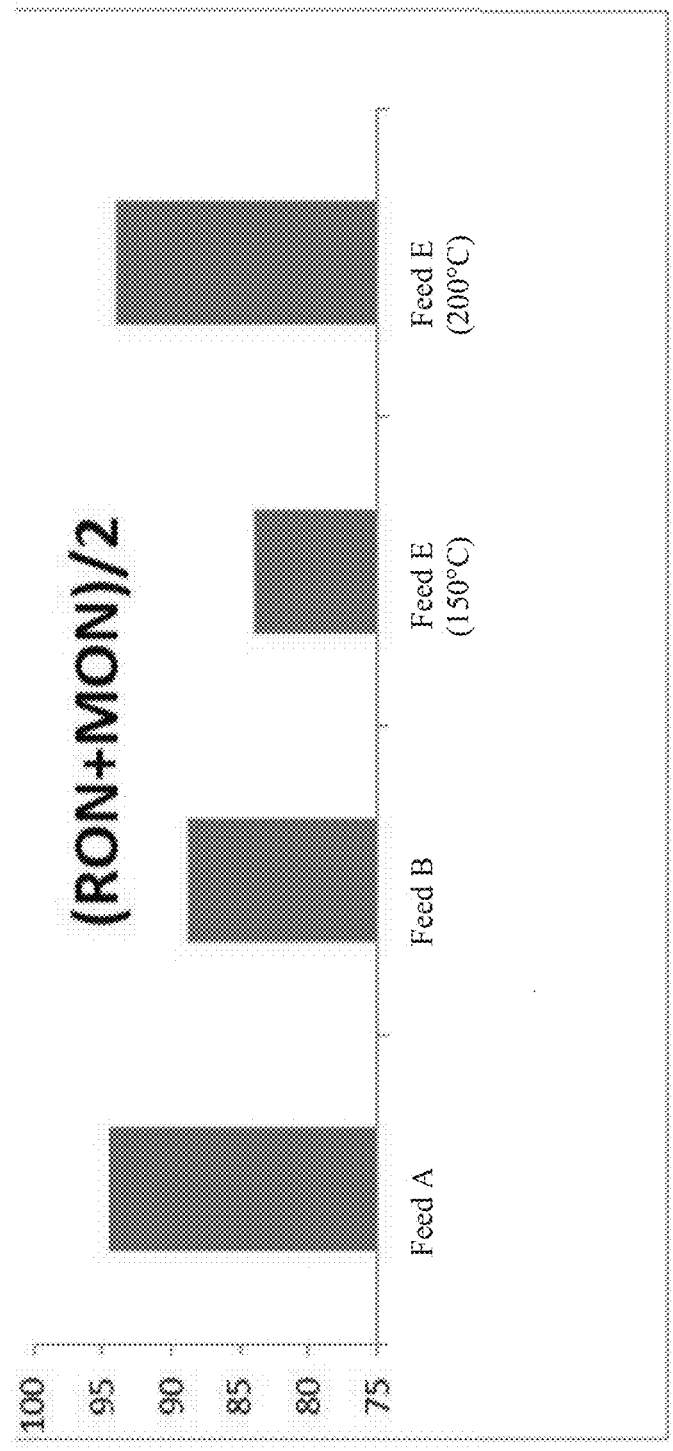
FIG. 5 shows octane of alkylation products using various feeds.

In addition to the amount of conversion, the resulting naphtha boiling range product from the reactions shown in FIG. 4 was analyzed for octane rating. FIG. 5 shows the (RON+MON)/2 values for the naphtha boiling range product from alkylation using Feeds A, B, and E. As shown in FIG. 5, the naphtha boiling range product generated by alkylation using Feed E at 200° C. had similar octane rating to the product from Feed A. This demonstrates that alkylation using only an initial isoparaffin feed can be used to generate an alkylate product with substantially the same octane rating as a conventional alkylation process, without requiring an olefin co-feed. It is believed that increasing the alkylation temperature from 150° C. to 170° C. would lead to a similar increase in octane rating for Feed B (isobutane and TBA without other oxygenates). More generally, it is believed that increasing the alkylation temperature for any of Feed B, C, or D would lead to an octane rating similar to the 90+ octane rating for Feed E in FIG. 5.

Additional Embodiments

Embodiment 1

A method for producing alkylate, comprising: exposing an isoparaffin-containing feed to oxidation conditions in the presence of oxygen to form an oxidation effluent comprising tertiary alcohol (optionally but preferably tertiary butyl alcohol), at least 0.5 wt % of the isoparaffins in the isoparaffin-containing feed being converted under the oxidation conditions; exposing at least a portion of the oxidation effluent to a solid acid catalyst under alkylation conditions to form an alkylation effluent, the at least a portion of the oxidation effluent comprising a molar ratio of isoparaffin to tertiary alcohol of about 5:1 to about 200:1.

Embodiment 2

The method of Embodiment 1, wherein the isoparaffin-containing feed comprises at least 80 wt % $C_{4-}$ isoparaffins, or at least 80 wt % $C_4$-$C_6$ isoparaffins, or at least 80 wt % isobutene, relative to a weight of the isoparaffin-containing feed (or at least 90 wt %, or at least 95 wt %, or at least 99 wt %)

Embodiment 3

The method of any of the above embodiments, wherein the oxidation effluent comprises a molar ratio of isoparaffin to tertiary alcohol of about 10:1 to about 100:1, or wherein the at least a portion of the oxidation effluent comprises at least 1.0 mol % t-butyl alcohol, or a combination thereof.

Embodiment 4

The method of any of the above embodiments, wherein the alkylation effluent comprises a naphtha boiling range portion having an octane rating, as determined by (RON+MON)/2, of at least 85, or at least 90, or 85 to 100, or 90 to 100.

Embodiment 5

The method of any of the above embodiments, wherein the isoparaffin-containing feed comprises a recycled portion of the alkylation effluent.

Embodiment 6

The method of any of the above embodiments, wherein the oxidation effluent further comprises water, one or more oxygenates, or a combination thereof, the one or more oxygenates optionally comprising methanol, acetone, or a combination thereof.

Embodiment 7

The method of any of the above embodiments, wherein the solid acid catalyst comprises a zeolite, a mixed metal oxide, a crystalline microporous material of the MWW framework type, or a combination thereof, the crystalline microporous material of the MWW framework type optionally being selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and mixtures thereof, preferably MCM-49, the MWW framework type material optionally containing up to 10% by weight of impurities of other framework structures.

Embodiment 8

The method of any of the above embodiments, wherein the solid acid catalyst further comprises an inorganic oxide binder in an amount of 0-90 weight %, or 0-50 weight %, or 0-20 weight %, or 0-10 weight %, or 1-90 weight %, or 1-50 weight %, or 1-20 weight %, or 1-10 weight %.

Embodiment 9

The method of Embodiment 8, wherein the inorganic oxide binder comprises alumina, or wherein the inorganic oxide binder is substantially free of amorphous alumina.

Embodiment 10

The method of Embodiment 8 or 9, wherein the inorganic oxide binder comprises silica.

Embodiment 11

The method of any of the above embodiments, wherein the alkylation conditions comprise a temperature of at least about 130° C., or at least about 170° C., or at least about 250° C.

Embodiment 12

The method of any of the above embodiments, wherein the alkylation effluent comprises a $C_8$ fraction comprising at least 50 wt % of 2,3,4, 2,3,3 and 2,2,4-trimethylpentane relative to a weight of the $C_8$ fraction, or at least 70 wt %.

Embodiment 13

A hydrocarbon product produced by alkylation of an isoparaffin feed comprising at least 60 mol % isobutane and 0.01 mol % to 0.5 mol % acetone on a dry basis, the hydrocarbon product further comprising a $C_8$ fraction comprising at least 50 wt % of 2,3,4, 2,3,3 and 2,2,4-trimethylpentane relative to a weight of the $C_8$ fraction, or at least 70 wt %.

Embodiment 14

A system for producing alkylate from an isoparaffin feed, comprising: an oxidation reactor comprising an isoparaffin feed inlet and an oxidation reactor outlet; an alkylation reactor comprising an alkylation reactor inlet, an alkylation reactor outlet, and a solid acid catalyst, the alkylation reactor inlet being in fluid communication with the oxidation reactor outlet, the solid acid catalyst optionally comprising a zeolite, a mixed metal oxide, a crystalline microporous material of the MWW framework type, or a combination thereof, the alkylation reactor inlet optionally being in direct fluid communication with the oxidation reactor outlet.

Embodiment 15

A hydrocarbon product produced according to the method of any of Embodiments 1-12.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The present invention has been described above with reference to numerous embodiments and specific examples. Many variations will suggest themselves to those skilled in this art in light of the above detailed description. All such obvious variations are within the full intended scope of the appended claims.

The invention claimed is:

1. A method for producing alkylate, comprising:
   exposing an isoparaffin-containing feed to oxidation conditions in the presence of oxygen to form an oxidation effluent comprising tertiary alcohol, water, methanol, acetone, and unreacted isoparaffins, at least 0.5 wt % of the isoparaffins in the isoparaffin-containing feed being converted under the oxidation conditions; and
   directly exposing at least a portion of the oxidation effluent to a solid acid catalyst under alkylation conditions to form an alkylation effluent, the at least a portion of the oxidation effluent comprising a molar ratio of isoparaffin to tertiary alcohol of about 5:1 to about 200:1.

2. The method of claim 1, wherein the isoparaffin-containing feed comprises at least 80 wt % $C_{4+}$ isoparaffins relative to a weight of the isoparaffin-containing feed.

3. The method of claim 1, wherein the isoparaffin-containing feed comprises at least 80 wt % $C_4$-$C_6$ isoparaffins relative to a weight of the isoparaffin-containing feed.

4. The method of claim 1, wherein the isoparaffin-containing feed comprises at least 80 wt % isobutane relative to a weight of the isoparaffin-containing feed.

5. The method of claim 1, wherein the oxidation effluent comprises a molar ratio of isoparaffin to tertiary alcohol of about 10:1 to about 100:1, or wherein the at least a portion of the oxidation effluent comprises at least 1.0 mol % t-butyl alcohol, or a combination thereof.

6. The method of claim 1, wherein the alkylation effluent comprises a naphtha boiling range portion having an octane rating, as determined by (RON+MON)/2, of at least 85.

7. The method of claim 1, wherein the isoparaffin-containing feed comprises a recycled portion of the alkylation effluent.

8. The method of claim 1, wherein the solid acid catalyst comprises a zeolite, a mixed metal oxide, a crystalline microporous material of the MWW framework topology, or a combination thereof.

9. The method of claim 1, wherein the solid acid catalyst comprises a crystalline microporous material of the MWW framework topology selected from the group consisting of MCM-22, PSH-3, SSZ-25, ERB-1, ITQ-1, ITQ-2, MCM-36, MCM-49, MCM-56, EMM-10, EMM-12, EMM-13, UZM-8, UZM-8HS, UZM-37, MIT-1, and mixtures thereof.

10. The method of claim 9, wherein the MWW framework topology material contains up to 10% by weight of impurities of other framework structures.

11. The method of claim 1, wherein the solid acid catalyst comprises a mixed metal oxide based on oxides of Fe/W/Zr, W/Zr, Ce/W/Zr, Cu/W/Zr, Mn/W/Zr, or a combination thereof.

12. The method of claim 1, wherein the solid acid catalyst further comprises an inorganic oxide binder.

13. The method of claim 12, wherein the inorganic oxide binder comprises alumina, or wherein the inorganic oxide binder is substantially free of amorphous alumina.

14. The method of claim 13, wherein the inorganic oxide binder comprises silica.

15. The method of claim 1, wherein the alkylation conditions comprise a temperature of at least about 130° C.

16. The method of claim 1, wherein the alkylation effluent comprises a $C_8$ fraction comprising at least 50 wt % of 2,3,4, 2,3,3 and 2,2,4-trimethylpentane relative to a weight of the $C_8$ fraction.

* * * * *